United States Patent [19]
Kato et al.

[11] Patent Number: 5,520,725
[45] Date of Patent: May 28, 1996

[54] DENTAL GLASS IONOMER CEMENT COMPOSITION

[75] Inventors: Shin-ichi Kato, Tokyo; Futoshi Fusejima, Kitamoto; Tohru Yoshikawa, Omiya, all of Japan

[73] Assignee: GC Corporation, Tokyo, Japan

[21] Appl. No.: 493,467

[22] Filed: Jun. 22, 1995

[30] Foreign Application Priority Data

Jul. 18, 1994 [JP] Japan ................... 6-186831

[51] Int. Cl.⁶ ................. A61K 6/08; C08F 2/48
[52] U.S. Cl. ............ 106/35; 433/228.1; 522/908; 523/115; 523/116
[58] Field of Search ............. 106/35; 523/115, 523/116; 433/228.1; 522/908

[56] References Cited

U.S. PATENT DOCUMENTS

| | | | |
|---|---|---|---|
| 4,775,592 | 10/1988 | Akahane et al. | 106/35 |
| 5,063,257 | 11/1991 | Akahane et al. | 523/116 |
| 5,112,880 | 5/1992 | Tsunekawa et al. | 523/116 |
| 5,314,474 | 5/1994 | Helms et al. | 623/16 |
| 5,332,429 | 7/1994 | Mitra et al. | 106/35 |
| 5,334,625 | 8/1994 | Ibsen et al. | 523/115 |
| 5,367,002 | 11/1994 | Huang et al. | 523/116 |
| 5,369,142 | 11/1994 | Culbertson et al. | 523/116 |
| 5,382,284 | 1/1995 | Arnold | 106/35 |
| 5,425,771 | 6/1995 | Helms et al. | 623/16 |
| 5,427,613 | 6/1995 | Arnold | 106/35 |

*Primary Examiner*—Anthony Green
*Attorney, Agent, or Firm*—Oblon, Spivak, McClelland, Maier & Neustadt

[57] ABSTRACT

The invention provides a dental glass ionomer cement composition comprising (a) an α-β unsaturated carboxylic acid polymer having a weight-average molecular weight lying in a specific range, (b) a polymerizable unsaturated organic compound having a $CH_2=C(R1)-COO$ group, (c) water, (d) an organic aromatic compound having a $-SO_2$ group, (e) a fluoroaluminosilicate glass powder having a mean particle size and specific gravity each lying in a specific range and capable of reacting with the component (a), and (f) a compound containing at least one element selected from the group consisting of aluminum, iron and tin. This composition can be cured either without recourse to conventional redox reaction systems or without exposure to visible light. It can be used with good-enough physical properties for dental therapy while it is harmless to the dental pulp, and can be stored over an extended period of time.

13 Claims, No Drawings

DENTAL GLASS IONOMER CEMENT COMPOSITION

BACKGROUND OF THE INVENTION

1. Field of the Invention

The present invention relates generally to a dental cement composition, and specifically to a dental glass ionomer cement composition. More specifically, the present invention is directed to a dental glass ionomer cement composition making use of the curing of a polymerizable unsaturated organic compound by a polymerization reaction in combination with the curing of a fluoroaluminosilicate glass powder with an $\alpha$-$\beta$ unsaturated carboxylic acid polymer by a neutralization reaction.

2. Prior Art

Many types of dental cements have been available in various applications. Typical of dental cements used so for in the art are zinc phosphate cement making use of the reaction of zinc oxide with phosphoric acid, polycarboxylate cement making use of the reaction of zinc oxide with a polycarboxylic acid, zinc oxide eugenol cement making use of the reaction of zinc oxide with eugenol, glass ionomer cement making use of fluoroaluminosilicate glass powders with a polycarboxylic acid, and resin cement making use of the polymerization of an acrylic monomer.

These dental cements have both merits and demerits. An ideal cement is not still found. For instance, the zinc phosphate cement shows no adhesion to dentine and has a stimulating action peculiar to phosphoric acid at the initial stage of curing; the polycarboxylate cement provides a cured material the final strength of which is low; the eugenol cement is used only for temporal sealing and attachment due to its low strength and its poor durability in the oral mouth, but it has a stimulating action inherent in eugenol; and the resin cement presents a problem in terms of bioaffinity.

In contrast, the glass ionomer cement is characterized in that it is of a very excellent bioaffinity and shows adhesion to dentine, and yields a cured material that is of semi-transparency and has a good-enough aesthetic appearance as well. In addition, fluorine contained in the glass is expected to make some contribution to dentine reinforcement. By taking advantage of many such characteristics, the glass ionomer cement has wide applications in the dental field, and are now used for the restoration and filling of caries cavities, the attachment of crowns, inlays, bridges and orthodontic bands, the lining of cavities, core building, and preventive filling.

A grave problem with the glass ionomer cement, however, is that its curing reaction is inhibited upon contact with moisture such as saliva at the initial stage of curing, resulting in some considerable degradation of its final physical properties. The reason is that the glass ionomer cement is easily affected by water, since the neutralization reaction between the polycarboxylic acid (an acidic component) and the fluoroaluminosilicate glass (a basic component) occurs in the presence of water. As the glass ionomer cement comes into contact with water at the initial stage of curing, its surface becomes brittle and cloudy, resulting an aesthetic problem. Many attempts have heretofore been made so as to eliminate this problem.

To achieve a sharp curing rate, for instance, Japanese Patent Publication No. 54(1979)-21858 and Japanese Patent Laid-Open No. 57(1982)-2210 teach the addition of a chelating agent and a fluorocomplex salt, respectively. Even according to these teachings, no complete solution can be provided to the above-mentioned problem or the degradation due to moisture of glass ionomer cement at the initial stage of curing.

To solve this problem, we have come up with a dental glass ionomer cement composition which comprises a liquid component containing a polymerizable unsaturated organic compound and a polymerization catalyst in addition to a conventional polyacrylic acid, so that it can be sharply cured by exposure to visible light, as disclosed in Japanese Patent Publication No. 6(1994)-27047.

In this glass ionomer cement, the neutralization reaction of the fluoroaluminosilicate glass powder with polyacrylic acid takes place at the initial stage of curing with the concurrence of the polymerization reaction of the unsaturated organic compound by exposure to light, so that it can cure quickly. This eliminates the problems in association with conventional glass ionomer cement compositions; their embrittlement or disintegration due to contact with moisture at the initial stage of curing. In addition, this cement can be more easily manipulated by curing by light than ever before. In particular, this glass ionomer cement composition are improved in terms of physical properties such as initial hardness, adhesion strength to dentine, bending or flexural strength, and transparency. Even in this cement, however, there are still some problems waiting solutions.

Among the advantages of the above-mentioned light curing type of unsaturated organic component-containing glass ionomer cement, there are improved physical properties such as initial hardness, flexural strength, adhesion strength to dentine and transparency in addition to use of visible light with which it can be more easily manipulated than ever before and resistance to embrittlement due to contact with moisture. However, this cement cannot be used for the purpose of attaching crowns or inlays to dentine at where irradiated light will not reach, because the polymerization of the unsaturated organic compound must be carried out by irradiating it with visible light. Another disadvantage of the light curing type of glass ionomer cement is that some limitation is placed on its curing depth achieved by exposure to visible light; that is, as when it is filled thick in a cavity, some cement layer tends to remain uncured due to incomplete polymerization in a deep portion. Rapid polymerization by exposure to light incurs an unavoidable contraction, which results in a gap or other cavity being formed between the cement and dentine. This, in turn, leads to detachment of the filler, or allows saliva to enter the gap or cavity, inducing secondary caries.

Thus, there has been a strong demand for glass ionomer cement which, while taking advantage of the unsaturated organic compound-containing cement, can be cured without recourse to exposure to visible light.

One possible way for dealing with this is to make use of a redox reaction in which a redox catalyst, typically a peroxide represented by benzoyl peroxide or KPS etc. takes part. However, the peroxide is unstable in glass ionomer cement, and so degrades immediately unless stored always at 4° C. or lower. This cement system is unsuitable for dental therapy because it evolves heat of considerable high temperature upon curing. The peroxide has a stimulating action on, and so harmful to, dentine. This accounts for a strong need for a glass ionomer cement composition containing a polymerizable unsaturated organic compound, which, even without recourse to use of a conventional redox reaction system and to exposure to visible light, can be cured into a material having physical properties good-enough for practical dental therapy, and can be stored over an extended period of time and harmless to dentine.

SUMMARY OF THE INVENTION

According to the present invention, there is provided a dental glass ionomer cement composition comprising:

(a) an α-β unsaturated carboxylic acid polymer having a weight-average molecular weight lying in the range of 5,000 to 40,000, (b) a polymerizable unsaturated organic compound having at least one group having the following general formula:

$CH_2=C(R1)-COO$ where R1 is H or $CH_3$ (c) water (d) an organic aromatic compound having at least one $-SO_2$ group, (e) a fluoroaluminosilicate glass powder which has a mean particle size lying in the range of 0.02 to 10 μm and a specific gravity lying in the range of 2.4 to 4.0 and is capable of reacting with said α-β unsaturated carboxylic acid polymer (a) having a weight-average molecular weight lying in the range of 5,000 to 40,000, and (f) a compound containing one or more than two elements selected from the group consisting of aluminum, iron and tin.

The glass ionomer cement composition according to the present invention enables the neutralization reaction between the fluoroaluminosilicate glass powder and the α-β unsaturated carboxylic acid polymer to take place with the concurrence of the rapid polymerization reaction of the polymerizable unsaturated organic compound with no need of exposure to visible light, so that it can have physical properties equivalent to or better than those of the conventional cement or a light curing type of glass ionomer cement. In addition, this can be stably stored over an extended period of time, and can be harmless to the dental pulp.

Preferably, the polymerizable unsaturated organic compound (b) having at least one group having the following general formula:

$CH_2=C(R1)-COO$ where R1 is H or $CH_3$ is incapable of reacting with the fluoroaluminosilicate glass powder (e) which has a mean particle size lying in the range of 0.02 to 10 μm and a specific gravity lying in the range of 2.4 to 4.0 and is capable of reacting with said α-β unsaturated carboxylic acid polymer (a) having a weight-average molecular weight lying in the range of 5,000 to 40,000. In other words, it is desired that the compound (b) is free from acid groups that react with the glass powder, for instance, carboxylic acid (—COOH), phosphorus-containing acid groups (—PO(OH)$_3$, —OPO(OH)$_2$, —PO(OH)OR, —OPO(OH)OR, etc.), sulfur-containing acid groups (—SO$_2$H, —SO$_3$H, —OSO$_3$H, etc.), boron-containing acid groups (—B(OH)$_2$, —OB(OH)$_2$, —B(OH)OR, —OB(OH)OR, etc.) or their salts. It is also desired that the compound (b) is free from acid groups that take part in acid-base reactions with the glass powder.

More specifically, the present invention provides a dental glass ionomer cement composition comprising:

(a) 5 to 100 parts by weight of an α-β unsaturated carboxylic acid polymer having a weight-average molecular weight lying in the range of 5,000 to 40,000, (b) 5 to 100 parts by weight of a polymerizable unsaturated organic compound having at least one group having the following general formula:

$CH_2=C(R1)-COO$ where R1 is H or $CH_3$ (c) 5 to 50 parts by weight of water (d) 0.01 to 5 parts by weight of an organic aromatic compound having at least one $-SO_2$ group, (e) 5 to 100 parts by weight of a fluoroaluminosilicate glass powder which has a mean particle size lying in the range of 0.02 to 10 μm and a specific gravity lying in the range of 2.4 to 4.0 and is capable of reacting with said α-β unsaturated carboxylic acid polymer (a) having a weight-average molecular weight lying in the range of 5,000 to 40,000, and (f) 0.01 to 100 parts by weight of a compound containing one or more than two elements selected from the group consisting of aluminum, iron and tin.

This dental glass ionomer cement composition enables the neutralization reaction between the fluoroaluminosilicate glass powder and the α-β unsaturated carboxylic acid polymer to take place with the concurrence of the rapid polymerization reaction of the polymerizable unsaturated organic compound with no need of exposure to visible light, so that it can have physical properties equivalent to or better than those of conventional cement or a light curing type of glass ionomer cement. In addition, this can be stably stored over an extended period of time, and can be harmless to the dental pulp.

Another aspect of the present invention is directed to using an additional ingredient (g) 0.01 to 5 parts by weight of a photopolymerization initiator for the rapid curing of the cement by exposure to visible light. The cement composition according to this aspect provides a so-called three-curing reaction system involving the rapid polymerization reaction of the polymerizable unsaturated organic compound, the neutralization reaction of the fluoroaluminosilicate glass powder with the α-β unsaturated carboxylic acid polymer, and the quick light-curing reaction by exposure to visible light. In this case, depending on necessity and purpose, light curing and chemical curing may be selectively used; this cement may find wider application. For instance, light curing may be used for cavity filling while chemical curing may be applied to the attachment of inlays or crowns. As can be understood from the examples to be given later, there is a very little difference in the physical properties of the dental glass ionomer cement composition between photo-curing and chemo-curing; that is, it can well stand up to practical use whether photo-cured or chemo-cured.

Preferably, the fluoroaluminosilicate glass powder (e) which has a mean particle size lying in the range of 0.02 to 10 μm and a specific gravity lying in the range of 2.4 to 4.0 and is capable of reacting with the α-β unsaturated carboxylic acid polymer (a) having a weight-average molecular weight lying in the range of 5,000 to 40,000 is a fluoroaluminosilicate glass powder which is coated on the surface with 0.01 to 20 parts by weight of an organic compound having a polymerizable ethylenic unsaturated double bond per 100 parts by weight of said glass powder, with said polymerizable ethylenic unsaturated double bond remaining because good-enough flatness is not obtained by polishing. Further, curing reaction to a liquid takes place slow and is not preferred. On the other hand, a glass powder having a mean particle size of less than 0.02 μm is in a form so fine that it can hardly be intermixed with the composition, making its physical properties worse. Particle size may be measured by a conventional means, and is represented in terms of mean value of long and short diameters. The true specific gravity of the glass powder used herein may be determined using a specific gravity bottle in the conventional manners. A departure from this range gives rise to a drop of glass reactivity, which may otherwise have an adverse influence on the physical properties of the cement composition.

Here a detailed account is given of the glass powder used in the present invention. It is preferable to use an aluminosilicate glass powder containing $Al^{3+}$, $Si^{4+}$, $F^-$ and $O^{2-}$ as major components and $Sr^{2+}$ and/or $Ca^{2+}$ as additional components. More preferably, the proportion of these major components is 10 to 21% by weight for $Al^{3+}$, 9 to 21% by weight for $Si^{4+}$, 1 to 20% by weight for $F^-$, and 10 to 34% by weight for $Sr^{2+}+Ca^{2+}$, all calculated with respect to the total weight of glass. The proportion of the major components has considerable influence on the handling parameters of cement such as curing rate, final strength and solubility as well as the physical properties of the cement. When the proportion of $Al^{3+}$ is lower than 10% by weight, the cement cures slowly with a lowering in its strength. A intact therein, whereby the physical properties of the cement is much more improved.

Preferably, the cement composition described above is used in a mixable paste form to obtain a dental glass ionomer cement which is of excellent mixability.

The α-β unsaturated carboxylic acid polymer (a) having a weight-average molecular weight lying in the range of 5,000 to 40,000 is understood to refer to a polymer of an α-β unsaturated mono- or di-carboxylic acid, and more illustratively mean a homo- or co-polymer of acrylic acid, methacrylic acid, 2-chloroacrylic acid, 3-chloroacrylic acid, aconitic acid, mesaconic acid, maleic acid, itaconic acid, fumaric acid, glutaconic acid and citraconic acid. These copolymers may be copolymers of α-β unsaturated carboxylic acids or an α-β unsaturated carboxylic acid with a component copolymerizable therewith. In this case, it is desired that the proportion of the α-β unsaturated carboxylic acid be 50% or more. The copolymerizable component used herein, for instance, may be acrylamide, acrylonitrile, methacrylic esters, acrylic acid salts, vinyl chloride, allyl chloride, and vinyl acetate. Particularly preferred among these α-β unsaturated carboxylic acid polymers is a homo- or co-polymer of acrylic acid or maleic acid. An α-β unsaturated carboxylic acid polymer, if having a weight-average molecular weight of 5,000 or less, offers a problem in that the resulting cured composition is of low strength and inferior durability as well as low adhesion strength to dentine. A polymer, if having a weight-average molecular weight of 40,000 or higher, provides a glass ionomer cement composition that shows too hard a consistency during mixing; in other words, much difficulty is involved in its mixing. Thus, the weight-average molecular weight of the α-β unsaturated carboxylic acid polymer used herein lies preferably in the range of 5,000 to 40,000.

The amount of the α-β unsaturated carboxylic acid polymer used in the composition of the present invention lies preferably in the range of 5 to 100 parts by weight. At 5 parts by weight or less there is sometimes a decrease in its adhesion to dentine which is one of the characteristic features of a glass ionomer cement. At 100 parts by weight or higher the cured composition or material often becomes poor in durability because of an increased solubility. Therefore, the preferred range of the α-β unsaturated carboxylic acid polymer used in the composition according to the present invention lies between 5 and 100 parts by weight with respect to the entire composition.

In the present invention no particular limitation is placed on the fluoroaluminosilicate glass powder used herein with the proviso that it has a mean particle size of 0.02 to 10 μm and a specific gravity of 2.4 to 4.0, and is capable of reacting with the α-β unsaturated carboxylic acid polymer (a) having a weight-average molecular weight of 5,000 to 40,000. As mentioned just above, the glass powder used herein has a mean particle size lying in the range of 0.02 to 10 μm. A glass powder, if having a mean particle size exceeding 10 μm, is in bad contact with the mouth area, glass powder containing more than 21% by weight of $Al^{3+}$ has much difficulty in glass making; the glass, if made, would be of poor transparency and so would have a less aesthetic appearance. When less than 9% by weight of $Si^{4+}$, making of the glass would become difficult. More than 24% by weight of $Si^{4+}$ is not practical because of the curing rate of cement becoming low, and makes the strength of the cement low, thus offering a durability problem. Less than 1% by weight of $F^-$ is not practical because the time needed for mixing or otherwise manipulating the cement becomes hard. More than 20% by weight of $F^-$ makes the final curing time of the cement too long, and makes the solubility of the cement in water too high and, hence, renders the durability of cement too worse. When the total amount of $Sr^{2+}$ and $Ca^{2+}$ is 10% by weight or less, no sharp curing of cement is achieved, resulting in an increase in the curing time of cement. In addition, glass making has difficulty. When the total amount of $Sr^{2+}$ and $Ca^{2+}$ exceeds 34% by weight, the time taken by mixing or otherwise manipulating the cement becomes too short to cure cement; that is, it is practically difficult to use the cement. In this case, again, the solubility of the cement in water increases, offering a durability problem.

For the reasons above mentioned, it is particularly preferable that the proportion of the major components of glass lies in the range above mentioned. The fluoroaluminosilicate glass used herein may be made by the conventional glass-making techniques known in the art. For instance, a glass material selected from the group consisting of silica, alumina, aluminum hydroxide, aluminum silicate, mullite, calcium silicate, strontium silicate, sodium silicate, aluminum carbonate, calcium carbonate, strontium carbonate, sodium carbonate, sodium fluoride, calcium fluoride, aluminum fluoride, strontium fluoride, aluminum phosphate, calcium phosphate, strontium phosphate and sodium phosphate may be weighed, melted at high temperatures of 1,000° C. or higher, cooled, and pulverized. In the composition of the present invention, the amount of this fluoroaluminosilicate glass powder lies preferably in the range of 5 to 100 parts by weight. At less than 5 parts by weight the cured material shows unsatisfactory physical properties, whereas at more than 100 parts by weight there is a reactivity drop.

It is here to be noted that the conventional inorganic fillers widely used for the so-called dental composite resin may be used in combination with the fluoroaluminosilicate glass powder. The filler used herein is understood to refer to the inorganic filler (h) which has a mean particle size of 0.02 to 10 μm and is incapable of reacting with the α-β unsaturated carboxylic acid polymer (a) having a weight-average molecular weight of 5,000 to 40,000. For instance, mention is made of quartz, colloidal silica, feldspar, alumina, strontium glass, barium glass, borosilicate glass, kaolin, talc, calcium carbonate, calcium phosphate, titania and barium sulfate. Composite fillers obtained by pulverizing inorganic filler-containing polymers may be used as well. These fillers may also be used in admixture.

In the present invention, it is preferable that the inorganic filler (h) which has a mean particle size of 0.02 to 10 μm and is incapable of reacting with the α-β unsaturated carboxylic acid polymer (a) having a weight-average molecular weight of 5,000 to 40,000 accounts for 0.01 to 50 parts by weight of the composition. At less than 0.01 part by weight it has no substantial effect on improving the physical properties of the composition, whereas at more than 50 parts by weight the composition has difficulty in mixing and decreases in physical properties.

If desired, the inorganic filler (h) may be used in combination with organic fillers such as methyl polyacrylate, methyl polymethacrylate, ethyl polyacrylate, ethyl polymethacrylate and an ethylene-vinyl acetate copolymer.

In the present invention, the polymerizable unsaturated organic compound having at least one $CH_2=C(R1)—COO$ group where R1 is H or $CH_2$ is understood to refer to a polymerizable unsaturated organic compound having an acryloyl or methacryloyl group, which is preferably incapable of reacting with the fluoroaluminosilicate glass powder. Preference is given to an ester of acrylic or methacrylic acid. For instance, acrylate or methacrylate compounds disclosed in Japanese Patent Publication No. 6(1994)-27047 may be used.

In the present invention, the esters of acrylic or methacrylic acid may be used alone or in combination of two or more. It is then particularly preferred that the total amount of urethane methacrylate, epoxy methacrylate and polyol methacrylate is 50% or more by weight relative to the total weight of the polymerizable unsaturated organic compound having at least one $CH_2=C(R1)—COO$ group where R1 is H or $CH_2$. The "urethane methacrylate" used herein is a general term of methacrylic acid esters having a urethane skeleton and, for instance, refers to the carbamate compounds already mentioned. The "polyol methacrylate" used herein is understood to refer to an ester of an at least divalent alcohol and methacrylic acid. The "epoxy methacrylate" used herein is a general term of methacrylic acid obtained by the reaction of an epoxy compound with methacrylic acid or methacrylate ester.

In the composition of the present invention, the polymerizable unsaturated organic compound having at least one $CH_2=C(R1)—COO$ group where R1 is H or $CH_2$ is preferably used in an amount lying in the range of 5 to 100 parts by weight. At 5 parts or less by weight the composition becomes poor in the initial curing property that is one of the chacteristic features of the present invenion, whereas at 100 parts or more by weight tile composition becomes poor in adhesion to dentine.

The organic aromatic compound having at least one $—SO_2$ group is herein understood to refer to an aromatic sulfinic acid or its metal salt, or an aromatic sulfonyl compound. For instance, mention is made of sodium p-toluenesulfinate, lithium p-toluenesufinate, benzenesulfinic acid, sodium benzenesulfinate, p-toluenesulfonyl chloride, p-toluene-sulfonyl fluoride, o-toluenesulfonyl isocyanate, p-toluenesulfonylhydrazide, p-toluenesulfonamide, p-toluene-sulfonylimidazol, p-toluenesulfonylcyanide, 2-(p-toluenesulfonyl)acetophenone, p-toluenesulfonyl-N-diethylamide, α-N, α-toluenesulfonyl-N-alginine, α-N, p-toluenesulfonyl-L-alginine methyl ester, p-toluenesulfonylmethyl isocyanate, p-toluene-sulfonyl-N-methyl-N-nitrosamide, N-(p-toluenesulfonyl)-L-phenylalanine, N-p-toluenesulfonyl-L-phenylalanylchloride, p-toluenesulfonylacetonitrile, 2-(p-toluenesulfonyl)acetophenone, toluene-3,4-disulfonyl chloride, benzene-sulfon-amide, benzenesulfohydroxysulfamic acid, benzenesulfonyl chloride, benzenesulfonyl isocyanate, benzenesulfon anilide, benzenesulfonchloroamide sodium, benzenesulfondichloroamide, benzenesulfonylhydrazide, benzenesulfonyl-N-methylamide, 2-phenylsulfonylacetophenone, diaminodiphenylsulfone, 4,4'-sulfonyldiphenol, sulfapyridine, sulfaerosol, sulfamethisol, ethylbenzenesulfonyl chloride, nitrobenzenesulfonyl chloride and nitrobenzenesulfonyl fluoride. It is here to be noted that the organic aromatic compound having at least one $—SO_2$ group may be used in the form of a hydrous salt.

For the composition of the present invention, it is preferable that the organic aromatic compound having at least one $—SO_2$ group is used in an amount of 0.01 to 5 parts by weight. At 0.01 parts or less by weight the cement does not cure. The organic aromatic compound, when used in an amount of 5 parts or more by weight, imparts no additional effect on the cured material and has also a risk of discoloration of the cured material.

The compound containing one or more than two element selected from the group consisting of aluminum, iron and tin is here understood to refer to the constitutional components of the fluoroaluminosilicate glass powder which has a mean particle size of 0.02 to 10 μm and a specific gravity of 2.4 to 4.0 and is capable of reacting with the α-β unsaturated carboxylic acid polymer having a weight-average molecular weight of 5,000 to 40,000. In addition to or instead of this, the compound may contain a metal salt containing one or more than two elements selected from the group consisting of aluminum, iron and tin. Examples of the metal salt used herein are aluminum chloride, aluminum oxide, aluminum acetate, aluminum salicylate, aluminum acrylate, aluminum oxalate, aluminum hydroxide, aluminum nitrate, aluminum carbonate, aluminum lactate, aluminum fluoride, aluminum sulfate, aluminum itaconate, aluminum phosphate, aluminum polychloride, aluminum iodide, aluminum acetylacetonate, aluminum bromide, aluminum butoxide, aluminum butylate, aluminum ethoxide, aluminum cyclohexanelactate, aluminum ethylhexoate, aluminum isopropoxide, aluminum laurate, aluminum oleate, potassium aluminum sulfate, aluminum stearate, aluminum triethoxide, aluminum triethylate, aluminum triisopropoxide, aluminum triisopropylate, barium aluminate, lithium aluminum hydride, sodium aluminate, iron oxide, iron chloride, iron sulfate, iron nitrate, iron hydroxide, iron ammonium sulfate, iron citrate, iron succinate, iron bromide, iron phosphate, iron dichloride, ethylenediamine iron, iron oxalate, iron lactate, iron ethylenediaminetetraacetate, iron 2-ethylhexoate, potassium ferrocyanide, potassium ferricyanide, acetylacetonatosodium ferrocyanide, iron alum, sodium iron citrate, sodium iron oxalate, iron ammonium sulfate, benzoylacetonatoiron, dicyclopentadienyliron, N,N-dimethyl-1-ferrocenylethylamine, iron decanoate, iron naphthenate, iron pentacarbonyl, iron nonacarbonyl, iron perchlorate, phthalocyanine iron, sodium pentacyanonitrosylferrate, sodium pentacyanoammineferrate, dicyano-bis(1,10-phenanthroline)iron, tris(1-phenyl-1,3-butanedionate)iron, tin oxide, tin chloride, tin acetate, tin phosphate, tin diphosphate, tin pyrophosphate, tin fluoride, tin iodide, tin oxalate, tin sulfate, tin bromide, tin tetrachloride, tin borofluoride, 2-ethylhexanoic acid tin salt, triphenyltin hydroxide, bis(tributyltin)oxide, di-n-butyltin diacetate, dibutyltin dichloride, di-n-butyltin dilaurate, dibutyltin oxide, hexabutyltin, bis(2-ethylhexanoic acid)dibutyltin, potassium stannate, sodium stannate, tetrabutyltin, tetraethyltin, tetramethyltin, tetraoctyltin, tetraphenyltin, tributyltin acetate, trimethyltin chloride, triethyltin chloride, triprolpyltin chloride, and tributyltin chloride. Optionally, these compounds may be used in combination of two or more. It is here to be understood that iron and tin compounds are often in ferrous and ferric forms and stannous and stannic forms, which may be used in the present invention. The compound containing one or more than two elements selected from the group consisting of aluminum, iron and tin may be used in the form of a hydrous salt.

In the composition of the present invention, it is preferred that the compound containing one or more than two elements selected from the group consisting of aluminum, iron and tin is used in an amount ranging from 0.01 to 100 parts by weight. The present composition, when containing 0.01 part or less of that compound, provides a cured material of insufficient physical properties or does not cure, whereas the present composition, when containing 100 parts or more of that compound, has difficulty in mixing or becomes poor in adhesion to dentine.

Water is an ingredient inevitable and essential for the dental glass ionomer cement composition of the present invention. One reason is that the reaction between the aluminosilicate glass and the $\alpha$-$\beta$ unsaturated carboxylic acid polymer proceeds in the presence of water. Another reason is that the dental glass ionomer cement composition of the present invention is bondable to the surface of a tooth in the presence of water. Where the composition of the present invention is used, it is essentially required that water exists. It is preferable that water is used in an amount ranging from 2 to 50 parts by weight. The composition of the present invention, when containing 50 parts or more by weight of water, provides a cured material of decreased physical properties, whereas the composition of the present invention, when containing 2 parts or less by weight of water, becomes poor in the adhesion to dentine that is one of the characteristic features of the glass ionomer cement.

To make the dental glass ionomer cement composition of the present invention curable upon exposure to light, a photopolymerization initiator may further be added thereto. To this end, various known photopolymerization initiators may be used, with carbonyl initiators being preferred. For instance, use may be made of photopolymerization initiators disclosed in Japanese Patent Publication No. 6(1994)-27047. If desired, these initiators may be used in combination of two or more. In the present composition, photopolymerization initiators should preferably be used in an amount ranging from 0.01 to 5 parts by weight. The present composition, when containing 0.01 part or less by weight of the initiator, fails to provide any sharp initial curing. Use of 5 parts or more by weight of the initiator does not always provide effect anticipated.

If required, the dental glass ionomer cement composition of the present invention may contain usual additives such as polymerization inhibitors and UV absorbers.

If desired, such polybasic carboxylic acids as disclosed in Japanese Patent. Publication No. 56(1981)-37965 may be added to the composition of the present invention so as to improve the strength of the final cured material.

The present invention includes the treatment of the surface of the fluoroaluminosilicate glass powder with the organic compound having a polymerizable ethylenic unsaturated double bond. This treatment may give rise to an increase in the final strength of the cured material, and makes some contribution to the intra-oral stability of cement. In a preferable embodiment, 100 parts by weight of the fluoroaluminosilicate glass are coated with 0.01 to 20 parts by weight of the organic compound having a polymerizable ethylenic unsaturated double bond. Within this range, some remarkable improvement in physical properties are often achieved. The organic compound having a polymerizable ethylenic unsaturated double bond, which is used for the treatment of the glass powder, is understood to refer to vinyl silane coupling agents such as vinyltrimethoxysilane, vinyltriethoxysilane, $\gamma$-methacryloxypropyltrimethoxysilane, $\gamma$-methacryloxypropylmethyldimethoxysilane, vinyltrichlorosilane and vinyl-tris(2-methoxyethoxy)silane, and unsaturated carboxylic acids such as methacrylic acid, acrylic acid and maleic acid. The polymerizable ethylenic double bond must remain intact even after the completion of the treatment. The organic compound having a polymerizable ethylenic unsaturated double bond may be applied to the surface of the fluoroaluminosilicate glass powder in the conventional manners. By way of example alone, the organic compound having a polymerizable ethylenic unsaturated double bond is dissolved or suspended in a suitable solvent. The resultant solution or suspension is then mixed with the aluminosilicate glass for reaction with the surface thereof. The subsequent drying gives the intended or desired glass powder. In the present invention, it is particularly preferable to use the silane coupling agent.

On the other hand, the dental glass ionomer cement composition of the present invention may be used in various formulations, e.g., powder-liquid, paste-liquid, and paste-paste formulations. These formulations have both merits and demerits, and paste formulations are preferable in view of ease with which they are mixed or otherwise manipulated. Whatever formulation is used, in view of storability it is difficult for all three ingredients, i.e., the $\alpha$-$\beta$ unsaturated carboxylic acid copolymer, fluoroaluminosilicate glass and water to coexist in either one part of the two-part formulation. More illustratively, a powder-liquid formulation may comprise one part consisting of the aluminosilicate glass powder and another part consisting of the $\alpha$-$\beta$ unsaturated carboxylic acid liquid containing an emulsion form of the polymerizable unsaturated organic compound at least one $CH_2=C(R1)$—COO group where R1 is H or $CH_2$. In this case, the $\alpha$-$\beta$ unsaturated carboxylic acid may be powdered for addition to the powder part. A paste-liquid formulation may be prepared by pasting the powder part of the powder-liquid formulation. In a paste-paste formulation, the ingredients may almost freely be divided into the two parts. For instance, the polymerizable unsaturated organic compound having at least one $CH_2=C(R1)$—COO group where R1 is H or $CH_2$ may be added to one paste part containing the fluoroaluminosilicate glass powder. In this case, it is preferable that this paste part is combined with another paste part composed mainly of an aqueous solution of the $\alpha$-$\beta$ unsaturated carboxylic acid polymer. Alternatively, the fluoroaluminosilicate glass powder may be pasted with an aqueous solution of polymer. Moreover, the polymerizable unsaturated organic compound having at least one $CH_2=C(R1)$—COO group where R1 is H or $CH_2$ may be emulsified and mixed with this paste part. In these cases, it is preferable that another paste part contains an aqueous solution composed predominantly of the $\alpha$-$\beta$ unsaturated carboxylic acid polymer. However, it is not preferable to incorporate the organic aromatic compound having at least one —$SO_2$ group, the water and the $\alpha$-$\beta$ unsaturated carboxylic acid polymer in one paste or liquid part, because the oxidation or decomposition of the organic aromatic compound having at least one —$SO_2$ group occurs. For pasting, water-soluble polymers may be used as subordinate components. For these water-soluble polymers, use may be made of those disclosed in Japanese Patent Publication No. 6(1994)-27047, for instance. These water-soluble polymers are preferably used in an amount ranging from 0.01 to 20 parts by weight. In the present invention, it is preferable that the paste has a viscosity of 2Pa.S or more because of ease with which it is mixed and otherwise manipulated.

EXAMPLES OF THE INVENTION

The present invention will now be explained in further detail with reference to examples.

Example 1

Aluminum oxide (23 g), anhydrous silicic acid (41 g), strontium fluoride (10 g), aluminum phosphate (13 g) and calcium phosphate (13 g) were well mixed together, and the mixture was held for 5 hours in a high temperature electric furnace maintained at temperature of 1,100° C. for glass melting. The melt was cooled, ball-milled for 10 hours, and then passed through a 200-mesh sieve (ASTM) to obtain glass powders. The glass powders (100 g) were well mixed with p-toluenesulfonylhydrazide (1 g) to prepare a cement powder part. Apart from this, polyacrylic acid (30 g) having a weight-average molecular weight of 20,000, di-2-methacryl-oxyethyl-hexamethylene dicarbamate (10 g), neopentyl glycol diacrylate (15 g) and distilled water (45 g) were mixed together under agitation for 60 minutes to obtain a homogenous cement liquid part. The cement powder part (2.5 g) was mixed with the liquid part (1.0 g) for 30 seconds.

The cured material was found to have a Vickers surface hardness of 21 Hv, as measured after the elapse of 10 minutes from the start of mixing, and was found to have a compressive strength of 150 MPa, a flexural strength of 30 MPa and a tensile adhesion strength of 7 MPa to bovine dentine, as measured after the elapse of 1 day. Thus, the glass ionomer composition of this example is found to cure rapidly, and provide a dental material having physical properties enough to meet practical use.

Example 2

Aluminum oxide (23 g), anhydrous silicic acid (41 g), strontium fluoride (10 g), aluminum phosphate (13 g) and calcium phosphate (13 g) were well mixed together, and the mixture was held for 5 hours in a high temperature electric furnace maintained at temperature of 1,100° C. for glass melting. The melt was cooled, ball-milled for 10 hours, and passed through a 200-mesh sieve (ASTM) to obtain glass powders. The glass powders (100 g) were well mixed with benzenesulfohydroxysulfamic acid (1 g) to prepare a cement powder part. Apart from this, polyacrylic acid (30 g) having a weight-average molecular weight of 20,000, di-2-methacryl-oxyethyl-hexamethylene dicarbamate (10 g), neopentyl glycol diacrylate (15 g) and distilled water (45 g) were mixed together under agitation for 60 minutes to obtain a homogenous cement liquid part. The cement powder part (2.5 g) was mixed with the liquid part (1.0 g) for 30 seconds.

The cured material was found to have a Vickers surface hardness of 23 Hv, as measured after the elapse of 10 minutes from the start of mixing, and was found to have a compressive strength of 145 MPa, a flexural strength of 27 MPa and a tensile adhesion strength of 7 MPa to bovine dentine, as measured after the elapse of 1 day. Thus, the glass ionomer composition of this example is found to cure rapidly, and become a dental material having practical-enough physical properties enough to meet practical use.

Example 3

Aluminum oxide (20 g), anhydrous silicic acid (45 g), calcium fluoride (8 g), aluminum phosphate (15 g) and strontium carbonate (12 g) were well mixed together, and the mixture was held for 5 hours in a high temperature electric furnace maintained at temperature of 1,200° C. for glass melting. The melt was cooled, ball-milled for 10 hours, and then passed through a 200-mesh sieve (ASTM) to obtain glass powders. The glass powders (100 g) were well mixed with p-toluenesulfonyl fluoride (1 g) and tin fluoride (1 g) to prepare a cement powder part. Apart from this, polyacrylic acid (20 g) having a weight-average molecular weight of 20,000, polymaleic acid (10 g) having a weight-average molecular weight of 8,000, di-2-methacryloxyethylhexamethylene dicarbamate (10 g), neopentyl glycol diacrylate (15 g) and distilled water (45 g) were mixed together under agitation for 60 minutes to obtain a homogenous cement liquid part. The cement powder part (2.5 g) was mixed with the liquid part (1.0 g) for 30 seconds.

The cured material was found to have a Vickers surface hardness of 23 Hv, as measured after the elapse of 10 minutes from the start of mixing, and was found to have a compressive strength of 145 MPa, a flexural strength of 27 MPa and a tensile adhesion strength of 8 MPa to bovine dentine, as measured after the elapse of 1 day. Thus, the glass ionomer composition of this example is found to cure rapidly, and provide a dental material having physical properties enough to meet practical use.

Example 4

Aluminum oxide (20 g), anhydrous silicic acid (45 g), calcium fluoride (8 g), aluminum phosphate (15 g) and strontium carbonate (12 g) were well mixed together, and the mixture was held for 5 hours in a high temperature electric furnace maintained at temperature of 1,200° C. for glass melting. The melt was cooled, ball-milled for 10 hours, and then passed through a 200-mesh sieve (ASTM) to obtain glass powders. The glass powders (100 g) were well mixed with a solution (20 g) of 10% vinyltriethoxysilane in ethyl alcohol in a mortar, and then dried at 110° C. for 2 hours in a steam dryer to obtain dried silane-treated powders. The dried silane-treated powders (100 g) was well mixed with benzenesulfonyl chloride (1 g) and iron citrate (0.5 g) in a dark room to prepare a cement powder part. Apart from this, polyacrylic acid (20 g) having a weight-average molecular weight of 18,000, polymaleic acid (10 g) having a weight-average molecular weight of 9,000, 2,2'-bis[3(4-phenoxy)-2-hydroxypropane-1-methacrylate]propane (15 g), di-1-methyl-2-methacryloxyethyl-hexane dicarbamate (25 g) and distilled water (30 g) were mixed together for 60 minutes to obtain a homogeneous cement liquid part. The cement powder part (2.5 g) was mixed with the liquid part (1.0 g) for 30 seconds.

The cured material was found to have a Vickers surface hardness of 21 Hv, as measured after the elapse of 10 minutes from the start of mixing, and was found to have a compressive strength of 139 MPa, a flexural strength of 24 MPa and a tensile adhesion strength of 6 MPa to bovine dentine, as measured after the elapse of 1 day. Thus, the glass ionomer composition of this example is found to cure rapidly, and provide a dental material having physical properties enough to meet practical use.

Example 5

Aluminum oxide (23 g), anhydrous silicic acid (41 g), strontium fluoride (10 g), aluminum phosphate (13 g) and calcium phosphate (13 g) were well mixed together, and the mixture was held for 5 hours in a high temperature electric furnace maintained at temperature of 1,100° C. for glass melting. The melt was cooled, ball-milled for 10 hours, and then passed through a 200-mesh sieve (ASTM) to obtain glass powders. The glass powders (100 g) were well mixed with benzenesulfohydroxysulfamic acid (1 g) and benzyldimethylketal (1 g) in a dark room to prepare a cement powder part. Apart from this, polyacrylic acid (30 g) having a weight-average molecular weight of 20,000, di-2-methacryloxyethyl-hexamethylene dicarbamate (10 g), neopentyl glycol diacrylate (15 g) and distilled water (45 g) were mixed together under agitation for 60 minutes to obtain a homogenous cement liquid part. The cement powder part (2.5 g) was mixed with the liquid part (1.0 g) for 30 seconds. After the elapse of 60 seconds from the start of mixing, the cement was cured by a 30-second irradiation with light from a visible light irradiator "LUXOR" (I.C.I., GB) having a tungsten halogen lamp.

The cured cement was found to have a Vickers surface hardness of 19 Hv, as measured just upon light curing. The cured cement was further found to have a Vickers surface hardness of 22 Hv, as measured after the elapse of 10 minutes from the start of mixing, indicating that this cement product can show sufficient physical properties even just after irradiation with light. The cement cured by exposure to light was also found to have a compressive strength of 140 MPa, a flexural strength of 30 MPa and a tensile adhesion strength of 9 MPa to bovine dentine, as measured after 1 day.

On the other hand, the cement parts were mixed at the same powder-liquid ratio, and then measured for Vickers surface hardness after the elapse of 10 minutes from the start of mixing without exposure to light. The result showed 23 Hv. The cement cured without exposure to light was found to have a compressive strength of 143 MPa, a flexural strength of 27 MPa and a tensile adhesion strength of 7 MPa to bovine dentine, as measured after 1 day. Thus, the glass ionomer composition of this example is found to provide a dental material having physical properties enough to meet practical use, whether cured in the presence or absence of light.

Example 6

Aluminum oxide (23 g), anhydrous silicic acid (41 g), strontium fluoride (10 g), aluminum phosphate (13 g) and calcium phosphate (13 g) were well mixed together, and the mixture was held for 5 hours in a high temperature electric furnace maintained at temperature of 1,100° C. for glass melting. The melt was cooled, ball-milled for 10 hours, and then passed through a 200-mesh sieve (ASTM) to obtain glass powders. The glass powders (100 g) were well mixed with benzenesulfohydroxysulfamic acid (1 g), tin fluoride (1 g) and benzyldimethylketal (1 g) in a dark room to prepare a cement powder part. Apart from this, polyacrylic acid (30 g) having a weight-average molecular weight of 14,000, di-2-methacryloxyethyl-hexamethylene dicarbamate (10 g), neopentyl glycol diacrylate (15 g) and distilled water (45 g) were mixed together for 60 minutes to obtain a homogenous cement liquid part. The cement powder part (2.5 g) was mixed with the liquid part (1.0 g) for 30 seconds. After the elapse of 60 seconds from the start of mixing, the cement was cured by a 30-second irradiation with light from a visible light irradiator "LUXOR" (I.C.I., GB) having a tungsten halogen lamp.

The cured cement was found to have a Vickers surface hardness of 21 Hv, as measured just upon light curing. The cured cement was further found to have a Vickers surface hardness of 24 Hv, as measured after the elapse of 10 minutes from the start of mixing, indicating that this cement product can show sufficient physical properties even just after irradiation with light. The cement cured by exposure to light was also found to have a compressive strength of 143 MPa, a flexural strength of 32 MPa and a tensile adhesion strength of 9 MPa to bovine dentine, as measured after 1 day.

On the other hand, the cement parts were mixed at the same powder-liquid ratio, and then measured for Vickers surface hardness after the elapse of 10 minutes from the start of mixing without exposure to light. The result showed 22 Hv. The cement cured without exposure to light was found to have a compressive strength of 144 MPa, a flexural strength of 30 MPa and a tensile adhesion strength of 7 MPa to bovine dentine, as measured after 1 day. Thus, the glass ionomer composition of this example is found to provide a dental material having physical properties enough to meet practical use, whether cured in the presence or absence of light.

Example 7

Aluminum oxide (23 g), anhydrous silicic acid (41 g), strontium fluoride (10 g), aluminum phosphate (13 g) and calcium phosphate (13 g) were well mixed together, and the mixture was held for 5 hours in a high temperature electric furnace maintained at temperature of 1,100° C. for glass melting. The melt was cooled, ball-milled for 10 hours, and then passed through a 200-mesh sieve (ASTM) to obtain glass powders. The glass powders (100 g) were well mixed with a solution (20 g) of 10% γ-methacryloxypropyltrimethoxysilane in ethyl alcohol in a mortar, and then dried at 110° C. for 2 hours in a steam dryer to obtain dried silane-treated powders. The dried silane-treated powders (100 g) was well mixed with p-toluenesulfonylhydrazide (1 g), camphor quinone (1 g) and aluminum oxalate (1 g) in a dark room to prepare a cement powder part. Apart from this, polyacrylic acid (20 g) having a weight-average molecular weight of 16,000, polymaleic acid (10 g) having a weight-average molecular weight of 7,000, di-2-methacryloxyethyl-hexamethylene dicarbamate (10 g), neopentyl glycol diacrylate (15 g) and distilled water (45 g) were mixed together for 60 minutes to obtain a homogeneous cement liquid part. The cement powder part (2.5 g) was mixed with the liquid part (1.0 g) for 30 seconds. After the elapse of 60 seconds from the start of mixing, the cement was cured by a 30-second irradiation with light from a visible light irradiator "LUXOR" (I.C.I., GB) having a tungsten halogen lamp.

The cured cement was found to have a Vickers surface hardness of 23 Hv, as measured just upon light curing. The cured cement was further found to have a Vickers surface hardness of 26 Hv, as measured after the elapse of 10 minutes from the start of mixing, indicating that this cement product can show sufficient physical properties even just after irradiation with light. The cement cured by exposure to light was also found to have a compressive strength of 145 MPa, a flexural strength of 30 MPa and a tensile adhesion strength of 10 MPa to bovine dentine, as measured after 1 day.

On the other hand, the cement parts were mixed at the same powder-liquid ratio, and then measured for Vickers surface hardness after the elapse of 10 minutes from the start of mixing without exposure to light. The result showed 22 Hr. The cement cured without exposure to light was found to have a compressive strength of 144 MPa, a flexural strength of 35 MPa and a tensile adhesion strength of 9 MPa to bovine dentine, as measured after 1 day. Thus, the glass ionomer composition of this example is found to provide a dental material having physical properties enough to meet practical use, whether cured in the presence or absence of light.

Example 8

Aluminum oxide (20 g), anhydrous silicic acid (45 g), calcium fluoride (8 g), aluminum phosphate (15 g) and strontium carbonate (12 g) were well mixed together, and the mixture was held for 5 hours in a high temperature electric furnace maintained at temperature of 1,200° C. for glass melting. The melt was cooled, ball-milled for 10 hours, and then passed through a 200-mesh sieve (ASTM) to obtain glass powders. The glass powders (100 g) were well mixed with a solution (20 g) of 10% vinyltriethoxysilane in ethyl alcohol in a mortar, and then dried at 110° C. for 2 hours in a steam dryer to obtain dried silane-treated powders. The dried silane-treated powders (100 g) was well mixed with p-toluenesulfonyl fluoride (1 g), α-alkylbenzoin (1 g) and iron chloride (0.5 g) in a dark room to prepare a cement powder part. Apart from this, polyacrylic acid (20 g) having a weight-average molecular weight of 22,000, polymaleic acid (10 g) having a weight-average molecular weight of 7,000, 2,2'-bis[3(4-phenoxy)-2-hydroxypropane-1-methacrylate]propane (15 g), neopentyl glycol diacrylate (25 g) and distilled water (30 g) were mixed together for 60 minutes to obtain a homogeneous cement liquid part. The cement powder part (2.8 g) was mixed with the liquid part (1.0 g) for 30 seconds. After the elapse of 60 seconds from the start of mixing, the cement was cured by a 30-second irradiation with light from a visible light irradiator "LUXOR" (I.C.I., GB) having a tungsten halogen lamp.

The cured cement was found to have a Vickers surface hardness of 27 Hv, as measured just upon light curing. The cured cement was further found to have a Vickers surface hardness of 30 Hv, as measured after the elapse of 10 minutes from the start of mixing, indicating that this cement product can show sufficient physical properties even just after irradiation with light. The cement cured by exposure to light was also found to have a compressive strength of 160 MPa, a flexural strength of 38 MPa and a tensile adhesion strength of 11 MPa to bovine dentine, as measured after 1 day.

On the other hand, the cement parts were mixed at the same powder-liquid ratio, and then measured for Vickers surface hardness after the elapse of 10 minutes from the start of mixing without exposure to light. The result showed 29 Hv. The cement cured without exposure to light was found to have a compressive strength of 162 MPa, a flexural strength of 36 MPa and a tensile adhesion strength of 7 MPa to bovine dentine, as measured after 1 day. Thus, the glass ionomer composition of this example is found to provide a dental material having physical properties enough to meet practical use, whether cured in the presence or absence of light.

Example 9

Aluminum oxide (20 g), anhydrous silicic acid (43 g), calcium fluoride (10 g), aluminum phosphate (12 g) and strontium carbonate (15 g) were well mixed together, and the mixture was held for 5 hours in a high temperature electric furnace maintained at temperature of 1,200° C. for glass melting. The melt was cooled, and ball-milled for 10 hours and then passed through a 200-mesh sieve (ASTM) to obtain glass powders. The glass powders (100 g) were well mixed with a solution (20 g) of 10% vinyl-tris(β-methoxyethoxy)silane in ethyl alcohol in a mortar, and then dried at 110° C. for 2 hours in a steam dryer to obtain dried silane-treated powders. The dried silane-treated powders (100 g) was well mixed with p-toluenesulfonyl fluoride (1 g) and camphor quinone (1 g) in a dark room to prepare a cement powder part. Apart from this, polyacrylic acid (20 g) having a weight-average molecular weight of 18,000, polymaleic acid (10 g) having a weight-average molecular weight of 9,000, 2,2'-bis[3(4-phenoxy)-2-hydroxypropane-1-methacrylate] propane (15 g), di-1-methyl-2-methacryloxyethyl-hexane dicarbamate (25 g) and distilled water (30 g) were mixed together for 60 minutes to obtain a homogeneous cement liquid part. The cement powder part (2.8 g) was mixed with the liquid part (1.0 g) for 30 seconds. After the elapse of 60 seconds from the start of mixing, the cement was cured by a 30-second irradiation with light from a visible light irradiator "LUXOR" (I.C.I., GB) having a tungsten halogen lamp.

The cured cement was found to have a Vickers surface hardness of 27 Hv, as measured just upon light curing. The cured cement was further found to have a Vickers surface hardness of 32 Hv, as measured after the elapse of 10 minutes from the start of mixing, indicating that this cement product can show sufficient physical properties even just after irradiation with light. The cement cured by exposure to light was also found to have a compressive strength of 165 MPa, a flexural strength of 37 MPa and a tensile adhesion strength of 10 MPa to bovine dentine, as measured after 1 day.

On the other hand, the cement parts were mixed at the same powder-liquid ratio, and then measured for Vickers surface hardness after the elapse of 10 minutes from the start of mixing without exposure to light. The result showed 30 Hr. The cement cured without exposure to light was found to have a compressive strength of 163 MPa, a flexural strength of 35 MPa and a tensile adhesion strength of 8 MPa to bovine dentine, as measured after 1 day. Thus, the glass ionomer composition of this example is found to provide a dental material having physical properties enough to meet practical use, whether cured in the presence or absence of light.

Example 10

Aluminum oxide (22 g), silicic anhydride (43 g), calcium fluoride (12 g), calcium phosphate (15 g) and strontium carbonate (8 g) were well mixed together, and the mixture was held for 5 hours in a high temperature electric furnace operating at temperature of 1,200° C. for glass melting. The melt was cooled, ball-milled for 10 hours, and passed through a 200-mesh sieve (ASTM) to obtain glass powders. The glass powders (100 g) were well mixed with p-toluenesulfonyl fluoride (2 g) and a 3% aqueous solution (30 g) of carboxymethylcellulose in a mortar to prepare a paste A. Apart from this, polyacrylic acid (20 g) having a weight-average molecular weight of 20,000, di-2-methacryloxyethyl-hexamethylene dicarbamate (45 g), neopentyl glycol diacrylate (10 g), distilled water (10 g) and fine silica sand powders (15 g) having a mean particle size of 2 μm were well mixed together for 60 minutes to prepare a homogeneous paste B. Paste A (1.0 g) was mixed with paste B (1.0 g) for 30 seconds. The cement was found to have a Vickers surface hardness of 18 Hv, as measured after the elapse of 10 minutes from the start of mixing. The cement was also found to have a compressive strength of 135 MPa, a flexural strength of 19 MPa and a tensile adhesion strength of 5 MPa to bovine dentine, as measured after 1 day. Thus, the glass ionomer composition of this example is found to cure rapidly, and provide a dental material having physical properties enough to meet practical use.

Example 11

Aluminum oxide (22 g), silicic anhydride (43 g), calcium fluoride (12 g), calcium phosphate (15 g) and strontium carbonate (8 g) were well mixed together, and the mixture was held for 5 hours in a high temperature electric furnace operating at temperature of 1,200° C. for glass melting. The melt was cooled, ball-milled for 10 hours, and passed through a 200-mesh sieve (ASTM) to obtain glass powders. The glass powders (100 g) were well mixed with benzenesulfohydroxysulfamic acid (2 g), tin chloride (1 g) and a 5% aqueous solution (30 g) of polyvinyl alcohol in a mortar to prepare a paste A. Apart from this, polyacrylic acid (15 g) having a weight-average molecular weight of 16,000, polymaleic acid (10 g) having a weight-average molecular weight of 8,000, di-2-methacryl-oxyethyl-hexamethylene dicarbamate (35 g), neopentyl glycol diacrylate (10 g), distilled water (15 g) and fine silica sand powders (15 g) having a mean particle size of 2 μm were well mixed together for 60 minutes to prepare a homogeneous paste B.

Paste A (1.0 g) was mixed with paste B (1.0 g) for 30 seconds. The cement was found to have a Vickers surface hardness of 19 Hv, as measured after the elapse of 10 minutes from the start of mixing. The cement was also found to have a compressive strength of 132 MPa, a flexural strength of 18 MPa and a tensile adhesion strength of 6 MPa to bovine dentine, as measured after 1 day. Thus, the glass ionomer composition of this example is found to cure rapidly, and provide a dental material having physical properties enough to meet practical use.

Example 12

Aluminum oxide (22 g), silicic anhydride (43 g), calcium fluoride (12 g), calcium phosphate (15 g) and strontium carbonate (8 g) were well mixed together, and the mixture was held for 5 hours in a high temperature electric furnace operating at temperature of 1,200° C. for glass melting. The melt was cooled, ball-milled for 10 hours, and passed through a 200-mesh sieve (ASTM) to obtain glass powders. The glass powders (100 g) were well mixed with benzenesulfohydroxysulfamic acid (2 g), tin chloride (1 g) and a 5% aqueous solution of polyvinyl alcohol in a mortar to make a paste A. Apart from this, polyacrylic acid (15 g) having a weight-average molecular weight of 16,000, polymaleic acid (10 g) having a weight-average molecular weight of 8,000, di-2-methacryloxy-ethyl-hexamethylene dicarbamate (35 g), neopentyl glycol diacrylate (10 g), distilled water (15 g), fine silica sand powders (15 g) having a mean particle size of 2 μm, camphor quinone (1 g) and thioxanthone (1 g) were well mixed together in a mortar in a dark room to make a paste B.

Paste A (1.0 g) was mixed with Paste B (1.0 g) for 30 seconds. After the elapse of 60 seconds from the start of mixing, the cement was cured by a 30-second irradiation with light from a visible light irradiator "LUXOR" (I.C.I., GB) having a tungsten halogen lamp. The cured cement was found to have a Vickers surface hardness of 19 Hv, as measured just upon light curing. The cured cement was further found to have a Vickers surface hardness of 21 Hv, as measured after the elapse of 10 minutes from the start of mixing, indicating that this cement product can show sufficient physical properties even just after irradiation with light. The cement cured by exposure to light was also found to have a compressive strength of 138 MPa, a flexural strength of 20 MPa and a tensile adhesion strength of 9 MPa to bovine dentine, as measured after 1 day.

On the other hand, the cement pastes were mixed at the same paste-paste ratio, and then measured for Vickers surface hardness after the elapse of 10 minutes from the start of mixing without exposure to light. The result showed 19 Hr. The cement cured without exposure to light was found to have a compressive strength of 133 MPa, a flexural strength of 18 MPa and a tensile adhesion strength of 6 MPa to bovine dentine, as measured after 1 day. Thus, the glass ionomer composition of this example is found to provide a dental material having physical properties enough to meet practical use, whether cured in the presence or absence of light.

Example 13

Aluminum oxide (20 g), silicic anhydride (41 g), calcium fluoride (15 g), calcium phosphate (10 g) and strontium carbonate (14 g) were well mixed together, and the mixture was held for 5 hours in a high temperature electric furnace operating at temperature of 1,200° C. for glass melting. The melt was cooled, ball-milled for 10 hours, and passed through a 200-mesh sieve (ASTM) to obtain glass powders. The glass powders (75 g) were well mixed with di-1-methyl-2-methacryloxyethyl-trimethyl dicarbamate (10 g), 10% aqueous solution (15 g) of polyvinyl pyrrolidone, benzenesulfonyl chloride (1 g) and iron citrate (0.5 g) in a mortar to make a paste A. Apart from this, polyacrylic acid (20 g) having a weight-average molecular weight of 30,000, polymaleic acid (10 g) having a weight-average molecular weight of 7,000, di-1-methyl-2-methacryloxyethyl-trimethylhexamethylene dicarbamate (50 g), distilled water (20 g), camphor quinone (1 g) and 2-chlorothioxanthone (1 g) were well mixed together for 60 minutes in a mortar in a dark room to make a paste B.

Paste A (2.0 g) was mixed with Paste B (1.0 g) for 30 seconds. After the elapse of 60 seconds from the start of mixing, the cement was cured by a 30-second irradiation with light from a visible light irradiator "LUXOR" (I.C.I., GB) having a tungsten halogen lamp. The cured cement was found to have a Vickers surface hardness of 22 Hv, as measured just upon light curing. The cured cement was further found to have a Vickers surface hardness of 25 Hv, as measured after the elapse of 10 minutes from the start of mixing, indicating that this cement product can show sufficient physical properties even just after irradiation with light. The cement cured by exposure to light was also found to have a compressive strength of 139 MPa, a flexural strength of 26 MPa and a tensile adhesion strength of 10 MPa to bovine dentine, as measured after 1 day.

On the other hand, the cement pastes were mixed at the same paste-paste ratio, and then measured of Vickers surface hardness after the elapse of 10 minutes from the start of mixing without exposure to light. The result showed 21 Hv. The cement cured without exposure to light was found to have a compressive strength of 133 MPa, a flexural strength of 18 MPa and a tensile adhesion strength of 6 MPa to bovine dentine, as measured after 1 day. Thus, the glass ionomer composition of this example is found to provide a dental material having physical properties enough to meet practical use, whether cured in the presence or absence of light.

Example 14

Aluminum oxide (20 g), silicic anhydride (41 g), calcium fluoride (15 g), calcium phosphate (10 g) and strontium carbonate (14 g) were well mixed together, and the mixture was held for 5 hours in a high temperature electric furnace operating at temperature of 1,200° C. for glass melting. The melt was cooled, ball-milled for 10 hours, and passed through a 200-mesh sieve (ASTM) to obtain glass powders. The glass powders (100 g) were well mixed with a solution (20 g) of 10% γ-methacryloxypropyltrimethoxysilane in ethyl alcohol in a mortar, and the mixture was dried at 110° C. for 2 hours in a steam dryer to obtain silane-treated glass powders. The silane-treated glass powders (75 g) were well mixed with 2,2,'-bis[3(4-phenoxy)-2-hydroxypropane-1-methacrylate]propane (15 g), di-2-methacryloxylethyl-hexamethylene dicarbamate (10 g); sodium p-toluenesulfinate (1 g) and tin oxalate (1 g) in a mortar to make a paste A. Apart from this, fine silica sand powders (100 g) having a mean particle size of 4 μm were well mixed with a solution (20 g) of 10% γ-methacryloxypropyltri-methoxysilane in ethyl alcohol in a mortar, and the mixture was dried at 110° C. for 2 hours in a steam dryer to obtain silane-treated silica sand powders. The silane-treated silica sand powders (50 g), polyacrylic acid (15 g) having a weight-average molecular weight of 30,000, polymaleic acid (10 g) having a weight-average molecular weight of 8,000, distilled water (25 g), benzyl(2-methoxyethyl)ketal (1 g) and α-alkylbenzoin (1 g) were well mixed together in a mortar in a dark room to make a paste B.

Paste A (2.0 g) was mixed with Paste B (1.0 g) for 30 seconds. After the elapse of 60 seconds from the start of mixing, the cement was cured by a 30-second irradiation with light from a visible light irradiator "LUXOR" (I.C.I., GB) having a tungsten halogen lamp. The cured cement was found to have a Vickers surface-hardness of 22 Hv, as measured just upon light curing. The cured cement was further found to have a Vickers surface hardness of 25 Hv, as measured after the elapse of 10 minutes from the start of mixing, indicating that this cement product can show sufficient physical properties even just after irradiation with light. The cement cured by exposure to light was also found to have a compressive strength of 142 MPa, a flexural strength of 28 MPa and a tensile adhesion strength of 8 MPa to bovine dentine, as measured after 1 day.

On the other hand, the cement pastes were mixed at the same paste-paste ratio, and then measured of Vickers surface hardness after the elapse of 10 minutes from the start of mixing without exposure to light. The result showed 20 Hv. The cement cured without exposure to light was found to have a compressive strength of 138 MPa, a flexural strength of 20 MPa and a tensile adhesion strength of 6 MPa to bovine dentine, as measured after 1 day. Thus, the glass ionomer composition of this example is found to provide a dental material having physical properties enough to meet practical use, whether cured in the presence or absence of light.

Example 15

Aluminum oxide (23 g), silicic anhydride (41 g), strontium fluoride (10 g), aluminum phosphate (13 g) and calcium phosphate (13 g) were well mixed together, and the mixture was held for 5 hours in a high temperature electric furnace operating at temperature of 1,100° C. for glass melting. The melt was cooled, ball-milled for 10 hours, and passed through a 200-mesh sieve (ASTM) to obtain glass powders. The glass powders (100 g) were well mixed with a solution (20 g) of 10% vinyltriethoxysilane in ethyl alcohol in a mortar, and the mixture was dried at 110° C. for 2 hours in a steam dryer to obtain silane-treated glass powders. The silane-treated glass powders (75 g) were well mixed with 2,2'-bis[3(4-phenoxy)-2-hydroxypropane-1-methacrylate]propane (15 g), di-2-methacryloxylethyl-hexamethylene dicarbamate (10 g), benzenesulfonamide (1 g), benzenesulfohydroxsulfamic acid (1g) and aluminum nitrate (1 g) in a mortar to make a paste A. Apart from this, fine silica sand powders (100 g) having a mean particle size of 4 μm were well mixed with a solution (20 g) of 10% vinyltriethoxysilane in ethyl alcohol in a mortar, and the mixture was dried at 110° C. for 2 hours in a steam dryer to obtain silane-treated silica sand powders. The silane-treated silica sand powders (50 g), an acrylic acid-itaconic acid copolymer (25 g) having a weight-average molecular weight of 24,000, distilled water (25 g), benzyldimethylketal (1 g) and methylthioxanthone (1 g) were well mixed together in a mortar in a dark room to make a paste B.

Paste A (2.0 g) was mixed with Paste B (1.0 g) for 30 seconds. After the elapse of 60 seconds from the start of mixing, the cement was cured by a 30-second irradiation with light from a visible light irradiator "LUXOR" (I.C.I., GB) having a tungsten halogen lamp. The cured cement was found to have a Vickers surface hardness of 17 Hv, as measured just upon light curing. The cured cement was further found to have a Vickers surface hardness of 20 Hv, as measured after the elapse of 10 minutes from the start of mixing, indicating that this cement product can show sufficient physical properties even just after irradiation with light. The cement cured by exposure to light was also found to have a compressive strength of 138 MPa, a flexural strength of 26 MPa and a tensile adhesion strength of 8 MPa to bovine dentine, as measured after 1 day.

On the other hand, the cement pastes were mixed at the same paste-paste ratio, and then measured for Vickers surface hardness after the elapse of 10 minutes from the start of mixing without exposure to light. The result showed 18 Hv. The cement cured without exposure to light was found to have a compressive strength of 135 MPa, a flexural strength of 24 MPa and a tensile adhesion strength of 7 MPa to bovine dentine, as measured after 1 day. Thus, the glass ionomer composition of this example is found to provide a dental material having physical properties enough to meet practical use, whether cured in the presence or absence of light.

Example 16

Aluminum oxide (23 g), silicic anhydride (41 g), strontium fluoride (10 g), aluminum phosphate (13 g) and calcium phosphate (13 g) were well mixed together, and the mixture was held for 5 hours in a high temperature electric furnace operating at temperature of 1,100° C. for glass melting. The melt was cooled, ball-milled for 10 hours, and passed through a 200-mesh sieve (ASTM) to obtain glass powders. The glass powders (100 g) were well mixed with a solution (20 g) of 10% vinyltrichlorosilane in ethyl alcohol in a mortar, and the mixture was dried at 110° C. for 2 hours in a steam dryer to obtain silane-treated glass powders. The silane-treated glass powders (70 g) were well mixed with di-2-methacryloxyethyl-hexamethylene dicarbamate (15 g), neopentyl glycol diacrylate (15 g), p-toluenesulfonyl fluoride (1 g) and iron oxalate (0.5 g) in a mortar to make a paste A. Apart from this, fine silica sand powders (100 g) having a mean particle size of 4 μm were well mixed with a solution (20 g) of 10% vinyltrichlorosilane in ethyl alcohol in a mortar, and the mixture was dried at 110° C. for 2 hours in a steam dryer to obtain silane-treated silica sand powders. The silane-treated silica sand powders (60 g), an acrylic acid-maleic acid copolymer (20 g) having a weight-average molecular weight of 18,000, distilled water (20 g) and P,P'-dichlorobenzyl (1 g) were well mixed together in a mortar in a dark room to make a paste B.

Paste A (1.5 g) was mixed with Paste B (1.0 g) for 30 seconds. After the elapse of 60 seconds from the start of mixing, the cement was cured by a 30-second irradiation with light from a visible light irradiator "LUXOR" (I.C.I., GB) having a tungsten halogen lamp. The cured cement was found to have a Vickers surface hardness of 16 Hv, as measured just upon light curing. The cured cement was further found to have a Vickers surface hardness of 19 Hv, as measured after the elapse of 10 minutes from the start of mixing, indicating that this cement product can show sufficient physical properties even just after irradiation with light. The cement cured by exposure to light was also found to have a compressive strength of 135 MPa, a flexural strength of 26 MPa and a tensile adhesion strength of 10 MPa to bovine dentine, as measured after 1 day.

On the other hand, the cement pastes were mixed at the same paste-paste ratio, and then measured for Vickers surface hardness after the elapse of 10 minutes from the start of mixing without exposure to light. The result showed 17 Hr. The cement cured without exposure to light was found to have a compressive strength of 138 MPa, a flexural strength of 24 MPa and a tensile adhesion strength of 8 MPa to bovine dentine, as measured after 1 day. Thus, the glass ionomer composition of this example is found to provide a dental material having physical properties enough to meet practical use, whether cured in the presence or absence of light.

Example 17

Aluminum oxide (23 g), silicic anhydride (41 g), strontium fluoride (10 g), aluminum phosphate (13 g) and calcium phosphate (13 g) were well mixed together, and the mixture was held for 5 hours in a high temperature electric furnace operating at temperature of 1,100° C. for glass melting. The melt was cooled, ball-milled for 10 hours, and passed through a 200-mesh sieve (ASTM) to obtain glass powders. The glass powders (100 g) were well mixed with a solution (20 g) of 10% vinyl-tris(β-methoxyethoxy)silane in ethyl alcohol in a mortar, and the mixture was dried at 110° C. for 2 hours in a steam dryer to obtain silane-treated glass powders. The silane-treated glass powders (65 g) were well mixed with di-2-methyl-2-methacryloxyethyl-hexamethylene dicarbamate (20 g), neopentyl glycol diacrylate (15 g), p-toluenesulfonyl fluoride (1 g) and aluminum carbonate (1 g) in a mortar to make a paste A. Apart from this, an acrylic acid-maleic acid copolymer (35 g) having a weight-average molecular weight of 18,000, an acrylic acid-itaconic acid copolymer (35 g) having a weight-average molecular weight of 10,000, distilled water (30 g) and camphor quinone (1 g) were well mixed together under agitation for 60 minutes in a dark room to make a paste B.

Paste A (2.0 g) was mixed with Paste B (1.0 g) for 30 seconds. After the lapse of 60 seconds from the start of mixing, the cement was cured by a 30-second irradiation with light from a visible light irradiator "LUXOR" (I.C.I., GB) having a tungsten halogen lamp. The cured cement was found to have a Vickers surface hardness of 18 Hv, as measured just upon light curing. The cured cement was further found to have a Vickers surface hardness of 21 Hv, as measured after the elapse of 10 minutes from the start of mixing, indicating that this cement product can show sufficient physical properties even just after irradiation with light. The cement cured by exposure to light was also found to have a compressive strength of 136 MPa, a flexural strength of 27 MPa and a-tensile adhesion strength of 9 MPa to bovine dentine, as measured after 1 day.

On the other hand, the cement pastes were mixed at the same paste-paste ratio, and then measured for Vickers surface hardness after the elapse of 10 minutes from the start of mixing without exposure to light. The result showed 16 Hv. The cement cured without exposure to light was found to have a compressive strength of 138 MPa, a flexural strength of 25 MPa and a tensile adhesion strength of 7 MPa to bovine dentine, as measured after 1 day. Thus, the glass ionomer composition of this example is found to provide a dental material having physical properties enough to meet practical use, whether cured in the presence or absence of light.

Comparative Example 1

Aluminum oxide (23 g), anhydrous silicic acid (41 g), strontium fluoride (10 g), aluminum phosphate (13 g) and calcium phosphate (13 g) were well mixed together, and the mixture was held for 5 hours in a high temperature electric furnace maintained at temperature of 1,100° C. for glass melting. The melt was cooled, ball-milled for 10 hours, and then passed through a 200-mesh sieve (ASTM) to obtain a glass powder part. Apart from this, polyacrylic acid (30 g) having a weight-average molecular weight of 20,000, di-2-methacryloxyethyl-hexamethylene dicarbamate (10 g), neopentyl glycol diacrylate (15 g) and distilled water (45 g) were mixed together under agitation for 60 minutes to obtain a homogenous cement liquid part. The cement powder part (2.5 g) was mixed with the liquid part (1.0 g) for 30 seconds. However, even after the elapse of 30 minutes from the start of mixing, the cement did not completely cure. The cement, upon coming into contact with water, was solubilized on the surface. The cement could not be measured for Vickers surface hardness. Nor could the physical properties of the cement be determined after 1 day.

Comparative Example 2

Aluminum oxide (23 g), anhydrous silicic acid (41 g), strontium fluoride (10 g), aluminum phosphate (13 g) and calcium phosphate (13 g) were well mixed together, and the mixture was held for 5 hours in a high temperature electric furnace maintained at temperature of 1,100° C. for glass melting. The melt was cooled, ball-milled for 10 hours, and passed through a 200-mesh sieve (ASTM) to obtain glass powders. The glass powders (100 g) were well mixed with camphor quinone (1 g) in a dark room to prepare a cement powder part. Apart from this, polyacrylic acid (30 g) having a weight-average molecular weight of 14,000, di-2-methacryloxyethyl-hexamethylene dicarbamate (10 g), neopentyl glycol diacrylate (15 g) and distilled water (45 g) were mixed together for 60 minutes to obtain a homogenous cement liquid part. The cement powder part (2.5 g) was mixed with the liquid part (1.0 g) for 30 seconds. After the elapse of 60 seconds from the start of mixing, the cement could not cure even after a 30-second irradiation with light from a visible light irradiator "LUXOR" (I.C.I., GB) having a tungsten halogen lamp.

On the other hand, the powder and liquid parts were mixed together at the same powder-liquid ratio. Even after the elapse of 30 minutes from the start of mixing, however, the cement did not completely cure when allowed to stand alone without exposure to light. The cement, upon coming into contact with water, was solubilized on the surface. The cement could not be measured for Vickers surface hardness. Nor could the physical properties of the cement be determined after 1 day.

Comparative Example 3

Aluminum oxide (23 g), anhydrous silicic acid (41 g), strontium fluoride (10 g), aluminum phosphate (13 g) and calcium phosphate (13 g) were well mixed together, and the mixture was held for 5 hours in a high temperature electric furnace maintained at temperature of 1,100° C. for glass melting. The melt was cooled, ball-milled for 10 hours, and passed through a 200-mesh sieve (ASTM) to obtain glass powders. The glass powders (100 g) were well mixed with a solution (20 g) of 10% γ-methacryloxy-propyltrimethoxysilane in ethyl alcohol in a mortar, and the mixture was dried at 110° C. for 2 hours in a steam dryer to prepare dried silane powders. The dried silane powders (100 g) was well mixed with benzyl(2-methoxyethyl)ketal (1 g) and α-alkylbenzoin (1 g) in a dark room to prepare a cement powder part. Apart from this, polyacrylic acid (20 g) having a weight-average molecular weight of 16,000, polymaleic acid (10 g) having a weight-average molecular weight of 7,000 (10 g), di-2-methacryloxyethyl-hexamethylene dicarbamate (10 g), neopentyl glycol diacrylate (15 g) and distilled water (45 g) were mixed together for 60 minutes to obtain a homogenous cement liquid part. The cement powder part (2.5 g) was mixed with the liquid part (1.0 g) for 30 seconds. After the lapse of 60 seconds from the start of mixing, the cement could not cure even after a 30-second irradiation with light from a visible light irradiator "LUXOR" (I.C.I., GB) having a tungsten halogen lamp.

On the other hand, the powder and liquid parts were mixed together at the same powder-liquid ratio. Even after the elapse of 30 minutes from the start of mixing, however, the cement did not completely cure when allowed to stand alone without exposure to light. The cement, upon coming into contact with water, was solubilized on the surface. The cement could not be measured for Vickers surface hardness. Nor could the physical properties of the cement be determined after 1 day.

Comparative Example 4

Aluminum oxide (22 g), anhydrous silicic acid (43 g), calcium fluoride (12 g), calcium phosphate (15 g) and strontium carbonate (8 g) were well mixed together, and the mixture was held for 5 hours in a high temperature electric furnace maintained at temperature of 1,200° C. for glass melting. The melt was cooled, ball-milled for 10 hours, and passed through a 200-mesh sieve (ASTM) to obtain glass powders. The glass powders (100 g) were well mixed with a 3% aqueous solution (30 g) of carbonmethylcelluose in a mortar to make a paste A. Apart from this, polyacrylic acid (20 g) having a weight-average molecular weight of 20,000, di-2-methacryloxyethyl-hexamethylene dicarbamate (45 g), neopentyl glycol diacrylate (10 g), distilled water (10 g) and fine silica sand powders (15 g) having a mean particle size of 2 μm were mixed together in a mortar to make a paste B.

Paste A (1.0 g) was mixed with paste B (1.0 g) for 30 seconds. Even after the lapse of 60 seconds from the start of mixing, the cement could not completely cure. The cement, upon coming into contact with water, was solubilized on the surface. The cement could not be measured for Vickers surface hardness. Nor could the physical properties of the cement be determined after 1 day.

Comparative Example 5

Aluminum oxide (23 g), anhydrous silicic acid (41 g), strontium fluoride (10 g), aluminum phosphate (13 g) and calcium phosphate (13 g) were well mixed together, and the mixture was held for 5 hours in a high temperatire electric furnace maintained at temperature of 1,100° C. for glass melting. The melt was cooled, ball-milled for 10 hours, and passed through a 200-mesh sieve (ASTM) to obtain glass powders. The glass powders (100 g) were well mixed with a solution (20 g) of 10% vinyltriethoxysilane in ethyl alcohol in a mortar, and the mixture was dried at 110° C. for 2 hours in a steam dryer to obtain silane-treated glass powders. The glass powders (75 g) was well mixed with 2,2'-bis[3(4-phenoxy)-2 -hydroxypropane-1-methacrylate] propane (15 g) and di-2-methacryloxyethyl-hexamethylene dicarbamate (10 g) in a mortar to make a paste A. Apart from this, fine silica sand powders (100 g) having a mean particle size of 4 μm were well mixed with a solution (20 g) of 10% vinyltriethoxysilane in ethyl alcohol in a mortar, and the mixture was dried at 110° C. for 2 hours in a steam dryer to obtain silane-treated silica sand powders. The silane-treated silica sand powders (50 g), an acrylic acid-itaconic acid copolymer (25 g) having a weight-average molecular weight of 24,000, distilled water (25 g), benzyldimethylketal (1 g) and methylthioxanthone (1 g) were well mixed together in a mortar in a dark room to make a paste B.

Paste A (2.0 g) was mixed with paste B (1.0 g) for 30 seconds. After the lapse of 60 seconds from the start of mixing, the cement could not cure even by a 30-second irradiation with light from a visible light irradiator "LUXOR" (I.C.I., GB) including a tungsten halogen lamp.

On the other hand, pastes A and B were mixed together at the same paste-paste ratio. Even after the elapse of 30 minutes from the start of mixing, however, the cement did not completely cure when allowed to stand alone without exposure to light. The cement, upon coming into contact with water, was solubilized on the surface. The cement could not be measured for Vickers surface hardness. Nor could the physical properties of the cement be determined after 1 day.

EFFECT OF THE INVENTION

The dental glass ionomer cement composition of the present invention is much more improved in terms of physical properties such as initial hardness, flexural strength and adhesion strength to dentine than the conventional glass ionomer cement, and so is expected to eliminate some problems of detachment, secondary caries, etc., which are serious in applications of cementing and core building when the conventional dental glass ionomer cement is used. The cured material is much better in semi-transparency and so aesthetic properties than ever before. Advantages of conventional glass ionomer cement, such as bioaffinity and long term fluoride release, remain intact.

If required depending on purpose, it is possible to make the composition of the present invention curable by irradiation with light. However, there is a very little difference in physical properties between the chemically cured cement composition and the cement composition cured by exposure to light. For instance, the light-cured cement composition may be selectively used for filling purposes, whereas the chemically cured composition may be selectively for cementing purposes. Thus, the dental glass ionomer cement composition of the present invention finds a wide range of applications and so makes a breakthrough in the art.

What is claimed is:

1. A dental glass ionomer cement composition consisting essentially of:
   (a) an α-β unsaturated carboxylic acid polymer having a weight-average molecular weight lying in the range of 5,000 to 40,000
   (b) a polymerizable unsaturated organic compound having at least one group having the following general formula:

$CH_2=C(R1)-COO$ where R1 is H or $CH_3$ (c) water
   (d) an organic aromatic compound having at least one $-SO_2$ group selected from the group consisting or aromatic sulfinic acids and metal salts thereof and aromatic sulfonyl compounds,
   (e) a fluoroaluminosilicate glass powder which has a mean particle size lying in the range of 0.02 to 10 μm and a specific gravity lying in the range of 2.4 to 4.0 and is capable of reacting with said α-β unsaturated carboxylic acid polymer (a) having a weight-average molecular weight lying in the range of 5,000 to 40,000, and
   (f) a compound selected from the group consisting of aluminum chloride, aluminum oxide, aluminum acetate, aluminum salicylate, aluminum acrylate, aluminum oxalate, aluminum hydroxide, aluminum nitrate, aluminum carbonate, aluminum lactate, aluminum fluoride, aluminum sulfate, aluminum itaconate, aluminum phosphate, aluminum polychloride, aluminum iodide, aluminum acetylacetonate, aluminum bromide, aluminum butoxide, aluminum butylate, aluminum ethoxide, aluminum cyclohexanelactate, aluminum ethylhexoate, aluminum isopropoxide, aluminum laurate, aluminum oleate, potassium aluminum sulfate, aluminum stearate, aluminum triethoxide, aluminum triethylate, aluminum triisopropoxide, aluminum triisopropylate, barium aluminate, lithium aluminum hydride, sodium aluminate, iron oxide, iron chloride, iron sulfate, iron nitrate, iron hydroxide, iron ammonium sulfate, iron citrate, iron succinate, iron bromide, iron phosphate, iron dichloride, ethylenediamine iron, iron oxalate, iron lactate, iron ethylenediaminetetraacetate, iron 2-ethylhexoate, potassium ferrocyanide, potassium ferricyanide, acetylacetonatosodium ferrocyanide, iron alum, sodium iron citrate, sodium iron oxalate, iron ammonium sulfate, benzoylacetonatoiron, dicyclopentadienyliron, N,N-dimethyl-1-ferrocenylethylamine, iron decanoate, iron naphthenate, iron pentacarbonyl, iron nonacarbonyl, iron perchlorate, phthalocyanine iron, sodium pentacyanonitrosylferrate, sodium pentacyanoammineferrate, dicyano-bis(1,10-phenanthroline) iron, tris(1-phenyl-1,3-butanedionate)iron, tin oxide, tin chloride, tin acetate, tin phosphate, tin diphosphate, tin pyrophosphate, tin fluoride, tin iodide, tin oxalate, tin sulfate, tin bromide, tin tetrachloride, tin borofluoride, 2-ethylhexanoic acid tin salt, triphenyltin hydroxide, bis(tributyltin)oxide, di-n-butyltin diacetate, dibutyltin dichloride, di-n-butyltin dilaurate, dibutyltin oxide, hexabutyltin, bis(2-ethylhexanoic acid)dibutyltin, potassium stannate, sodium stannate, tetrabutyltin, tetraethyltin, tetramethyltin, tetraoctyltin, tetraphenyltin, tributyltin acetate, trimethyltin chloride, triethyltin chloride, tripropyltin chloride, and tributyltin chloride.

2. The dental glass ionomer cement composition as recited in claim 1, wherein said polymerizable unsaturated organic compound (b) is incapable of reacting with said fluoroaluminosilicate glass powder (e).

3. A dental glass ionomer cement composition consisting essentially of:
   (a) 5 to 100 parts by weight of an α-β unsaturated carboxylic acid polymer having weight-average molecular weight lying in the range of 5,000 to 40,000,
   (b) 5 to 100 parts by weight of a polymerizable unsaturated organic compound having at least one group having the following formula:

$CH_2=C(R1)-COO$ where R1 is H or $CH_3$ (c) 5 to 50 part as by weight of water
   (d) 0.01 to 5 parts by weight of an organic aromatic compound having at least one $-SO_2$ group selected from the group consisting of aromatic sulfinic acids and metal salts thereof and aromatic sulfonyl compounds,
   (e) 5 to 100 parts by weight of a fluoroaluminosilicate glass powder which has a mean particle size lying in the range of 0.02 to 10 μm and a specific gravity lying in the range of 2.4 to 4.0 and is capable of reacting with said α-β unsaturated carboxylic acid polymer (a) having a weight-average molecular weight lying in the range of 5,000 to 40,000, and
   (f) 0.01 to 100 parts by weight of a compound selected from the group consisting of aluminum chloride, aluminum oxide, aluminum acetate, aluminum salicylate, aluminum acrylate, aluminum oxalate, aluminum hydroxide, aluminum nitrate, aluminum carbonate, aluminum lactate, aluminum fluoride, aluminum sulfate, aluminum itaconate, aluminum phosphate, aluminum polychloride, aluminum iodide, aluminum acetylacetonate, aluminum bromide, aluminum butoxide, aluminum butyrate, aluminum ethoxide, aluminum cyclohexanelactate, aluminum ethylhexoate, aluminum isopropoxide, aluminum laurate, aluminum oleate, potassium aluminum sulfate, aluminum stearate, aluminum triethoxide, aluminum triethylate, aluminum triisopropoxide, aluminum triisopropylate, barium aluminate, lithium aluminum hydride, sodium aluminate, iron oxide, iron chloride, iron sulfate, iron nitrate, iron hydroxide, iron ammonium sulfate, iron citrate, iron succinate, iron bromide, iron phosphate, iron dichloride, ethylenediamine iron, iron oxalate, iron lactate, iron ethylenediaminetetraacetate, iron 2-ethylhexoate, potassium ferrocyanide, potassium ferricyanide, acetylacetonatosodium ferrocyanide, iron alum, sodium iron citrate, sodium iron oxalate, iron ammonium sulfate, benzoylacetonatoiron, dicyclopentadienyliron, N,N-dimethyl-1-ferrocenylethylamine, iron decanoate, iron naphthenate, iron pentacarbonyl, iron nonacarbonyl, iron perchlorate, phthalocyanine iron, sodium pentacyanonitrosylferrate, sodium pentacyanoammineferrate, dicyano-bis(1,10-phenanthroline) iron, tris(1-phenyl-1,3-butanedionate)iron, tin oxide, tin chloride, tin acetate, tin phosphate, tin diphosphate, tin pyrophosphate, tin fluoride, tin iodide, tin oxalate, tin sulfate, tin bromide, tin tetrachloride, tin borofluoride, 2-ethylhexanoic acid tin salt, triphenyltin hydroxide, bis(tributyltin)oxide, di-n-butyltin diacetate, dibutyltin dichloride, di-n-butyltin dilaurate, dibutyltin oxide, hexabutyltin, bis(2-ethylhexanoic acid) dibutyltin, potassium stannate, sodium stannate, tetrabutyltin, tetraethyltin, tetramethyltin, tetraoctyltin, tetraphenyltin, tributyltin acetate, trimethyltin chloride, triethyltin chloride, tripropyltin chloride, and tributyltin chloride.

4. The dental glass ionomer cement composition as recited in any one of claims 1 or 2 further consisting essentially of an additional component (g) that is a photopolymerization initiator.

5. A dental glass ionomer cement composition consisting essentially of:

(a) 5 to 100 parts by weight of an α-β unsaturated carboxylic acid polymer having a weight-average molecular weight lying in the range of 5,000 to 40,000, (b) 5 to 100 parts by weight of a polymerizable unsaturated organic compound having at least one group having the following general formula:

$CH_2$—$C(R1)$—$COO$ where R1 is H or $CH_3$ (c) 5 to 50 parts by weight of water (d) 0.01 to 5 parts by weight of an organic aromatic compound having at least one —$SO_2$ group selected from the group consisting of aromatic sulfinic acids and metal salts thereof and aromatic sulfonyl compounds, (e) 5 to 100 parts by weight of a fluoroaluminosilicate glass powder which has a mean particle size lying in the range of 0.02 to 10 μm and a specific gravity lying in the range of 2.4 to 4.0 and is capable of reacting with said α-β unsaturated carboxylic acid polymer (a) having a weight-average molecular weight lying in the range of 5,000 to 40,000, (f) 0.01 to 100 parts by weight of a compound selected from the group consisting of aluminum chloride, aluminum oxide, aluminum acetate, aluminum salicylate, aluminum acrylate, aluminum oxalate, aluminum hydroxide, aluminum nitrate, aluminum carbonate, aluminum lactate, aluminum fluoride, aluminum sulfate, aluminum itaconate, aluminum phosphate, aluminum polychloride, aluminum iodide, aluminum acetylacetonate, aluminum bromide, aluminum butoxide, aluminum butylate, aluminum ethoxide, aluminum cyclohexanelactate, aluminum ethylhexoate, aluminum isopropoxide, aluminum laurate, aluminum oleate, potassium aluminum sulfate, aluminum stearate, aluminum triethoxide, aluminum triethylate, aluminum triisopropoxide, aluminum triisopropylate, barium aluminate, lithium aluminum hydride, sodium aluminate, iron oxide, iron chloride, iron sulfate, iron nitrate, iron hydroxide, iron ammonium sulfate, iron citrate, iron succinate, iron bromide, iron phosphate, iron dichloride, ethylenediamine iron, iron oxalate, iron lactate, iron ethylenediaminetetraacetate, iron 2-ethylhexoate, potassium ferrocyanide, potassium ferricyanide, acetylacetonatosodium ferrocyanide, iron alum, sodium iron citrate, sodium iron oxalate, iron ammonium sulfate, benzoylacetonatoiron, dicyclopentadienyliron, N,N-dimethyl-1-ferrocenylethylamine, iron decanoate, iron naphthenate, iron pentacarbonyl, iron nonacarbonyl, iron perchlorate, phthalocyanine iron, sodium pentacyanonitrosylferrate, sodium pentacyanoammineferrate, dicyano-bis(1,10-phenanthroline) iron, tris(1-phenyl-1, 3-butanedionate) iron, tin oxide, tin chloride, tin acetate, tin phosphate, tin diphosphate, tin pyrophosphate, tin fluoride, tin iodide, tin oxalate, tin sulfate, tin bromide, tin tetrachloride, tin borofluoride, 2-ethylhexanoic acid tin salt, triphenyltin hydroxide, bis(tributyltin)oxide, di-n-butyltin diacetate, dibutyltin dichloride, di-n-butyltin dilaurate, dibutyltin oxide, hexabutyltin, bis(2-ethylhexanoic acid)dibutyltin, potassium stannate, sodium stannate, tetrabutyltin, tetraethyltin, tetramethyltin, tetraoctyltin, tetraphenyltin, tributyltin acetate, trimethyltin chloride, triethyltin chloride, tripropyltin chloride, and tributyltin chloride, and (g) 0.01 to 5 parts by weight of a photopolymerization initiator.

6. The dental glass ionomer cement composition as recited in any one of claims 1 or 5, wherein said α-β unsaturated carboxylic acid polymer (a) is a copolymer or homopolymer of at least one monomer selected from the group consisting of acrylic acid, methacrylic acid, 2-chloroacrylic acid, 3-chloroacrylic acid, aconitic acid, mesaconic acid, maleic acid, itaconic acid, fumaric acid, glutaconic acid and citraconic acid.

7. The dental glass ionomer cement composition as recited in any one of claims 1 or 5, wherein said α-β unsaturated carboxylic acid polymer (a) is a homopolymer of acrylic acid or maleic acid, or a copolymer containing acrylic acid or maleic acid.

8. The dental glass ionomer cement composition as recited in any one of claims 1 or 5, wherein said polymerizable unsaturated organic compound (b) is an ester of acrylic acid or methacrylic acid.

9. The dental glass ionomer cement composition as recited in any one of claims 1 or 5, wherein said fluoroaluminosilicate glass powder (e) is a fluoroaluminosilicate glass powder comprising $Al^{3+}$, $Si^{4+}$, $F^-$, $O^{2-}$ and at least one of $Sr^{2+}$ or $Ca^{2+}$.

10. The dental glass ionomer cement compositions as recited in any one of claims 1 or 5, wherein said fluoraluminosilicate glass powder (e) is a fluoroaluminosilicate glass powder having a surface coated with 0.01 to 20 parts by weight of an organic compound having a polymerizable ethylenic unsaturated double bond, per 100 parts by weight of said glass powder.

11. The dental glass ionomer cement composition as recited in any one of claims 1 or 5, further consisting essentially of (h) 0.01 of 50 parts by weight of an inorganic filler having a mean particle size of 0.02 to 10 μm and incapable of reacting with said α-β unsaturated carboxylic acid polymer (a).

12. The dental glass ionomer cement composition as recited in claim 11, wherein said inorganic filler (h) is an inorganic filler having a surface coated with 0.01 to 20 parts by weight of an organic compound having a polymerizable ethylenic unsaturated double bond, per 100 parts by weight of said inorganic filler.

13. The dental glass ionomer cement composition as recited in any one of claims 1 or 5, further consisting essentially of 0.01 to 20 parts by weight of a water-soluble polymer (i).

* * * * *